US005245097A

United States Patent [19]

Wu

[11] Patent Number: 5,245,097
[45] Date of Patent: Sep. 14, 1993

[54] ETHYLENE OLIGOMERIZATION

[75] Inventor: An-hsiang Wu, Bartlesville, Okla.

[73] Assignee: Phillips Petroleum Company, Bartlesville, Okla.

[21] Appl. No.: 809,774

[22] Filed: Dec. 18, 1991

[51] Int. Cl.[5] .............................. C07C 2/26; C07C 2/36
[52] U.S. Cl. ..................................... 585/513; 585/514; 585/517; 585/518; 585/523
[58] Field of Search ............... 585/513, 514, 517, 518, 585/523

[56] References Cited

U.S. PATENT DOCUMENTS

| 3,452,115 | 6/1969 | Schneider | 260/683.15 |
|---|---|---|---|
| 3,513,218 | 5/1970 | Faltings et al. | 260/683.15 |
| 3,689,588 | 9/1972 | Dunn | 585/513 |
| 3,992,323 | 11/1976 | Yoo et al. | 252/430 |
| 4,362,650 | 12/1982 | Chauvin et al. | 585/513 |
| 4,482,640 | 11/1984 | Knudsen et al. | 502/155 |
| 4,487,847 | 12/1984 | Kundsen | 502/155 |
| 4,518,814 | 5/1985 | Knudsen et al. | 585/523 |
| 4,528,415 | 7/1985 | Knudsen | 585/527 |
| 4,709,112 | 11/1987 | Sato et al. | 585/513 |
| 4,992,610 | 2/1991 | Sato et al. | 585/513 |

Primary Examiner—Asok Pal
Attorney, Agent, or Firm—William R. Sharp

[57] ABSTRACT

An ethylene oligomerization process is provided wherein ethylene is contacted with an organonickel(II) compound, a phosphine compound and an alkylaluminum compound in a first solvent to produce a precursor reaction mixture, followed by contacting ethylene with the precursor reaction mixture and a fluorinated organoacid, preferably in a second solvent, to produce a product reaction mixture comprising the desired oligomerization product. Results of the process can be optimized by employing phosphorus-containing additives as described herein.

21 Claims, No Drawings

ETHYLENE OLIGOMERIZATION

This invention relates to a process for oligomerizing ethylene to an oligomerization product. The term "oligomerization product" as used herein and in the appended claims is defined as including olefinic oligomers of ethylene, i.e. $C_nH_{2n}$ where $n=4, 6, 8, 10, \ldots$ The simpler notation of $C_n$ will be used hereafter to denote such oligomers.

Olefins, including α-olefins or 1-olefins, have become very important products in the chemical industry. Through hydroformylation, copolymerization and arylation/sulfonation, the 1-olefins become components of plasticizers, solvents, plastics, surfactants, synthetic lubricants, fatty acids and detergents. Production of 1-olefins by oligomerizing ethylene has been previously investigated to a considerable extent, such as in processes employing nickel catalyzed oligomerization, but further improvement would be desirable in regard to achieving a combination of high productivity, high selectivity to 1-olefins and a desirable distribution (primarily $C_4$'s–$C_{10}$'s) of ligomers in the oligomerization product.

It is, therefore, an object of the invention to provide an improved process for oligomerizing ethylene which achieves the above-mentioned desired combination of results.

The above object is achieved by a process for oligomerizing ethylene to an oligomerization product comprising the steps of: (a) contacting ethylene, an organonickel(II) compound (having nickel in a valence state of +2), a phosphine compound of the formula $PR_3$ where R independently represents H or a $C_1$ to $C_{20}$ hydrocarbyl radical and where at least one R is not H, and an alkylaluminum compound having at least one $C_1$ to $C_{12}$ alkyl radical and at least one aluminum atom per molecule, wherein the ethylene is in a gaseous phase and the organonickel(II) compound, phosphine compound and alkylaluminum compound are in a first solvent and in a liquid phase, thereby producing a precursor reaction mixture in a liquid phase; and (b) contacting, after step (a), ethylene in a gaseous phase, the precursor reaction mixture, and a fluorinated organoacid in a liquid phase, thereby producing a product reaction mixture in a liquid phase comprising the oligomerization product. The fluorinated organoacid in step (b) is preferably in a second solvent.

Suitable organonickel(II) compounds include bis(cyclopentadienyl) nickel(II), bis(pentamethylcyclopentadienyl) nickel(II), nickel(II) 2-ethylhexanoate, nickel(II) acetylacetonate, nickel(II) trifluroacetylacetonate, nickel(II) hexafluoroacetylacetonate, nickel(II) acetate, nickel(II) hydroxyacetate, nickel(II) stearate, nickel(II) cyclohexanebutylrate and nickel(II) oxalate. The first six listed organonickel(II) compounds, particularly nickel(II) acetylacetonate, are preferred. Each of such preferred organonickel(II) compounds have a nickel atom bonded to at least one organic ligand by means of a main valence bond and a coordination bond. In addition, a hydrated form of the organonickel(II) compound is preferred as being less expensive and more stable than the anhydrous form of such compound, although the anhydrous form can be employed if desired.

Suitable phosphine compounds of the formula $PR_3$, where R independently represents H or a $C_1$ to $C_{20}$ hydrocarbyl radical and where at least one R is not H, include cyclohexylphosphine, dicyclohexylphosphine, tricyclohexylphosphine, triethylphosphine, triisopropylphosphine, triisobutylphosphine, tri-n-butylphosphine, tri-t-butylphosphine, diphenylphosphine, triphenylphosphine, diphenylcyclohexylphosphine, diethylphenylphosphine, ortho-tolyldiphenylphosphine, di(ortho-tolyl)phenylphosphine and tribenzylphosphine. Tricyclohexylphosphine and triisopropylphosphine are preferred as giving the optimum distribution of oligomers in the $C_4$–$C_{10}$ range.

Suitable alkylaluminum compounds having at least one $C_1$ to $C_{12}$, preferably $C_1$ to $C_6$, alkyl radical and at least one aluminum atom per molecule include triisobutylaluminum, triethylaluminum, trimethylaluminum, di-isobutylaluminum chloride, di-isobutylaluminum hydride, diethylaluminum chloride and triethyldialuminum trichloride. Particularly preferred in accordance with the invention is a trialkylaluminum compound of the formula $AlR'_3$ where R' is the above-mentioned alkyl radical, such as triisobutylaluminum, triethylaluminum or trimethylaluminum. Triethylaluminum is most preferred.

The preferred fluorinated organoacid is a fluorinated carboxylic acid of the formula $R''COOH$ where R'' represents a $C_1$ to $C_{10}$, preferably $C_1$ to $C_3$, hydrocarbyl radical having at least one fluorine (F) atom. Suitable fluorinated carboxylic acids include trifluoroacetic acid, heptaflurobutyric acid, difluoroacetic acid, and pentafluoropropionic acid. The preferred fluorinated carboxylic acid is trifluoroacetic acid. Fluorinated organoacids also within the scope of certain broad aspects of the invention are a fluorinated dicarboxylic acid such as perfluroadipic acid, and fluorinated sulfonic acids such as trifluoromethanesulfonic acid and heptafluoroethanesulfonic acid.

The preferred molar ratio of (i) the phosphine compound, (ii) the alkylaluminum compound, and (iii) the fluorinated organoacid, respectively, to the organonickel(II) compound are as follows: (i) about 0.1–5 to 1, most preferably about 0.8–1.2 to 1; (ii) about 1–10 to 1, most preferably about 1.5–2.5 to 1; and (iii) about 1–20 to 1, most preferably about 5–7 to 1.

The first solvent, as recited in step (a) above, is selected from the group consisting of: a saturated hydrocarbon or fluorinated hydrocarbon of the formula $C_nH_{2n+2-x}F_x$ where $n=4, 5, 6, 7$ or 8 and $x=0, 1$ or 2; and an aromatic hydrocarbon or fluorinated hydrocarbon of the formula $C_6H_{6-n}(R''')_n$ where $n=0, 1, 2, 3$, or 4 and R''' independently represents F or a $C_1$ to $C_6$ alkyl radical or fluorinated alkyl radical. Suitable saturated hydrocarbons or fluorinated hydrocarbons include isobutane, isopentane, neohexane, n-heptane, n-pentane, n-hexane, octane, isooctane, perfluoralkanes and fluorinated alkanes. Suitable aromatic hydrocarbons or fluorinated hydrocarbons include α,α,α-trifluorotoluene, 2-fluorotoluene, 3-fluorotoluene, 4-fluorotoluene, fluorobenzene, difluorobenzene (1,2;1,3;1,4), difluorotoluene (2,4;2,5;2,6;3,4), toluene, benzene, ethylbenzene and xylene (o, p, m). The aromatic hydrocarbons, particularly fluorinated, are preferred as optimizing productivity.

The second solvent, as recited above in the preferred embodiment of step (b), is selected from the group consisting of: a saturated hydrocarbon or fluorinated hydrocarbon as described above; an aromatic hydrocarbon or fluorinated hydrocarbon also as described above; and an alcohol of the formula $(R^{iv})_3COH$ where $R^{iv}$ independently represents H, F or a $C_1$ to $C_{12}$ alkyl, cycloalkyl, aryl, alkaryl, or aralkyl radical and where at least one $R^{iv}$ is neither H nor F. The alcohol is preferred as optimizing selectivity to 1-olefins in conjunction with good productivity. Suitable alcohols include 1-propanol, 1-butanol, 2-methyl-2-butanol (t-amyl alcohol), 1-pentanol, 2-pentanol, 1-hexanol, 1-octanol and 1-decanol.

The weight ratio of the first solvent to the combination of the organonickel(II) compound, phosphine compound and alkylaluminum compound, and also the weight ratio of the second solvent to the fluorinated organoacid, can be in the broad range of about $1-10^6$ to 1, most preferably in the range of about 5–10,000 to 1. The amount of solvent employed depends upon the cost, ease of oligomerization product recovery therefrom, reactor size, and other practical considerations.

The particular procedure by which the various reagents are contacted as in (a) and (b) above can take a variety of forms as will be apparent from subsequently described examples.

In accordance with step (a), the organonickel(II) compound, phosphine compound, and alkylaluminum compound in the first solvent and in liquid phase can be contacted with ethylene in gaseous phase in a first vessel by agitating the liquid phase therein and pressuring the first vessel with the ethylene to a predetermined pressure. Most preferably, the organonickel(II) compound, phosphine compound and first solvent are first added to the first vessel, followed by addition of the alkylaluminum compound.

In accordance with step (b), the acid in the second solvent can be added to a second vessel, and either the precursor reaction mixture resulting from step (a) can be transferred from the first vessel to the second vessel or the acid in the second solvent can be transferred to the first vessel. In either case, the precursor reaction mixture, acid and second solvent are preferably agitated in whichever vessel receives all liquid reagents and such vessel is pressured with ethylene to a predetermined reaction pressure. Most preferably, the acid is contacted with ethylene in the second vessel prior to contacting with the precursor reaction mixture.

The vessel in which step (b) is carried out can be an autoclave or other similar pressure reactor, and the vessel in which step (a) is carried out can be such a reactor or an associated addition vessel, depending on the particular procedure employed.

Pressure and temperature conditions in steps (a) and (b) are such that the ethylene is in a gaseous phase and the organonickel(II) compound, phosphine compound and alkylaluminum compound as in the first solvent and the acid as in the second solvent are in the liquid phase. More specifically, step (a) is preferably carried out at a pressure of about 5 to 5000 psig and a temperature of about $-100°$ C. to about 50° C., most preferably at a pressure of about 20 to about 1000 psig and a temperature of about 15° C. to about 35° C. (generally ambient temperature conditions). Step (b) is preferably carried out at a pressure of about 5 to about 5000 psig and a temperature of about 0° C. to about 125° C., most preferably at a pressure of about 200 to about 1000 psig and a temperature of about 20° C. to about 50° C.

With respect to time, step (a) is preferably carried out for a time of about 1 minute to about 6 hours, most preferably about 15 minutes to about 3 hours. Step (b) is preferably carried out for a time of about 1 minute to about 15 hours, most preferably about 15 minutes to about 5 hours.

The oligomerization product as contained in the product reaction mixture resulting from step (b) can be separated and recovered from the product reaction mixture by conventional means such as fractional distillation. As demonstrated in examples to follow, the oligomerization product contains a desirable distribution of primarily $C_4$–$C_{10}$ oligomers.

Results in accordance with the invention can be even further optimized in certain respects by employing a phosphorus-containing compound as an additive to the basic process and as will be described further below. Such a phosphorus-containing compound can be a phosphine compound as described previously, or a phosphite compound of the formula $P(OR^v)_3$ where $R^v$ independently represents H or a $C_1$ to $C_{20}$ hydrocarbyl radical and where at least one $R^v$ is not H. Suitable phosphite compounds include di-n-butylphosphite, diethylphosphite, diisopropylphosphite, tri-n-butylphosphite, triethylphosphite, trimethylphosphite, tri-neo-pentylphosphite, triphenylphosphite, triisopropylphosphite, tricyclohexylphosphite and tris(ortho-tolyl)phosphite.

An above-mentioned phosphorus-containing compound can be dissolved in the second solvent in addition to the acid. The molar ratio of such a phosphorus-containing compound to the organonickel(II) compound is preferably about 0.1–10 to 1, most preferably about 0.5–5 to 1. Such a phosphorus-containing compound as present in the second solvent in addition to the acid serves to improve selectivity to 1-olefins, as will be demonstrated in a subsequent example.

An above-mentioned phosphorus-containing compound can also be added to the product reaction mixture at a predetermined time following commencement of step (b). After addition of such a phosphorus-containing compound, it is preferably allowed to react with the product reaction mixture under oligomerization reaction conditions for a brief period of time of, for example, about 1 to about 15 minutes. The molar ratio of the phosphorous-containing compound, as added to the product reaction mixture, to the organonickel(II) compound is preferably about 0.5–10 to 1, most preferably about 1–6 to 1. Addition of the phosphorus-containing compound to the product reaction mixture as described above serves to decrease or stop isomerization of desired 1-olefins in the product reaction mixture to other isomers during distillation of the product reaction mixture. This will also be demonstrated in a subsequent example. Triphenylphosphite is particularly preferred as effectively stopping isomerization during distillation and as serving to cause at least a portion of nonoligomer components of the product reaction mixture to precipitate out. Such precipitate can be easily removed by filtration prior to distillation, thus facilitating separation and recovery of the oligomerization product from the product reaction mixture.

Many variations of the invention are possible in light of the above teachings. For example, although the invention is described above in terms of a batchwise process, it is within the scope of certain broad aspects of the invention to employ a continuous process wherein ethylene is passed continuously into a reaction zone while product reaction mixture containing the oligomerization product is concomitantly withdrawn therefrom.

Examples are set forth below which further illustrate the invention but which should not be construed to limit the invention in any manner.

Each example employed at least one 300 mL stainless steel (316SS) Autoclave Engineers stirred tank autoclave, hereafter denoted simply as a reactor. Other equipment employed in individual examples will be referenced in those examples. It is understood that the contents of such reactor(s) in the following examples are being agitated, typically at a slow agitation of about 300 rpm during purging of the reactor or addition of various reagents to the reactor, and at a normal agitation of about 1600 rpm at all other times.

Product analysis was performed on approximately 5 gram samples with an HP 5890 II GC-FID Spectrometer equipped with a capillary DB-1 (60 m) column. The column was operated at 30° C. for 5 minutes, followed by a 15° C./minute increase to 285° C. which was held for 13 minutes. Detection was obtained using a flame ionization detector in the area percent mode. Selectivity and weight percent distribution, discussed further below, were determined from spectra as recorded by the spectrometer.

In the following examples, results are reported in terms of productivity, selectivity to 1-olefins and weight percent distribution of oligomerization product. Productivity is defined as the grams of oligomerization product produced per gram of Ni per hour, and was calculated in each example based on grams of ethylene reacted. Selectivity to 1-olefins is given in terms of the weight percent of various fractions ($C_n$, n=4,6,8, ...) of the oligomerization product which is 1-olefin. The distribution of the oligomerization product is given as the weight percent of the various fractions of the total oligomerization product.

EXAMPLE I

This example illustrates ethylene oligomerization employing a variety of hydrocarbon solvents and several different phosphine compounds.

The oligomerization reaction, including 8 runs, was carried out in the reactor described above. The reactor was first purged with nitrogen for 10 minutes followed by addition of 47 mL of a freshly distilled hydrocarbon solvent listed in Table I, 0.278 g (0.945 mmol) of nickel-(II) acetylacetonate hydrate, and a phosphine compound (0.945 mmol) listed in Table I. 1 mL of a 1.9M solution of triethylaluminum (1.90 mmol) in toluene was then added through an addition port on the reactor. The reactor was then sealed, purged with ethylene several times (5 or 6), and then pressured to 200 psig with ethylene for 30 minutes. All of the above described steps were undertaken at ambient temperature (about 25° C.).

Trifluoroacetic acid (0.649 g; 5.69 mmol) and 2 mL of the freshly distilled hydrocarbon solvent listed in Table I were added to a 40 mL addition vessel, equipped with a pressure gauge, by the use of a syringe. The vessel was immediately sealed and pressured to 700 psig with ethylene. The contents of the addition vessel, including the ethylene, were then transferred to the reactor at the end of the above-mentioned 30 minute period through its addition valve. Reaction proceeded immediately, evidenced by the rise in reaction temperature. The reaction temperature was controlled at 40° C. by use of external cooling water. The internal reactor pressure was maintained at 700 psig and the reaction was continued for 1 hour.

At the end of the reaction period, a sample of the product reaction mixture was taken from the reactor through its sample valve into a 50 mL pressure sample tube, and was analyzed as described above. The resulting selectivity and weight distribution data, along with corresponding phosphine compound, solvent and productivity, are set forth in Table I. It is understood that runs 2–6 use the same phosphine compound as run 1. A similar notation is used in subsequent examples.

TABLE I

| Run | Phosphine | Hydrocarbon Solvent | Productivity | Selectivity wt % of 1-$C_n$ (n = 4,6,8,10) | Distribution wt % of $C_n$ (n = 4,6,8,10,12,14 and higher) |
|---|---|---|---|---|---|
| 1 | TCHP[a] | Benzene | 513 | 68,67,67,65 | 17,25,25,20,9,4 |
| 2 | | Toluene | 1322 | 74,72,72,71 | 33,28,19,12,6,2 |
| 3 | | p-Xylene | 1258 | 81,80,78,75 | 32,29,21,10,6,2 |
| 4 | | Flurobenzene | 1396 | 78,75,72,71 | 26,28,22,14,7,3 |
| 5 | | Trifluorotoluene | 2133 | 64,63,63,61 | 35,34,20,9,2,0 |
| 6 | | n-heptane | 275 | 71,69,69,68 | 37,30,19,8,4,2 |
| 7 | DCHP[b] | Toluene | 809 | 85,83,82,80 | 60,26,10,3,1,0 |
| 8 | CHP[c] | Toluene | 208 | 94,93,92,92 | 61,26,10,3,0,0 |

[a]Tricyclohexylphosphine
[b]Dicyclohexylphosphine
[c]Cyclohexylphosphine

The results shown in Table I indicate that the productivity is very high, up to 2,133 g/g/hr, when trifluorotoluene was used as a solvent. Also shown in the Table is the selectivity to 1-olefins of the $C_4$, $C_6$, $C_8$ and $C_{10}$ fractions. The selectivity is in the range of 63–94%. The distribution of the oligomerization product varies among the solvents, but is mostly lower than $C_{12}$ olefins.

EXAMPLE II

This example shows that selectivity to 1-olefins of the oligomerization product can be improved by using an alcohol solvent in conjunction with trifluoroacetic acid.

The runs were carried out the same as those described in Example I except for the following: trifluoroacetic acid was added to 35 ml of an alcohol solvent listed in Table II instead of 2 ml of a hydrocarbon solvent; 35 ml of toluene was used in the reactor instead of 47 ml; and the reactor was pressured with ethylene to 50 psig instead of 200 psig.

TABLE II

| Run | Phosphine | Alcohol Solvent | Productivity | Selectivity wt % 1-$C_n$ (n = 4,6,8,10) | Distribution wt % $C_n$ (n = 4,6,8, 10,12,14 and higher) |
|---|---|---|---|---|---|
| 9 | TCHP[a] | 1-propanol | 1114 | 96,95,97,96 | 36,29,17,10,5,3 |
| 10 | | 1-butanol | 1164 | 96,94,96,94 | 32,29,18,11,6,4 |
| 11 | | 1-pentanol | 1095 | 96,95,96,96 | 32,27,19,12,6,4 |

TABLE II-continued

| Run | Phosphine | Alcohol Solvent | Productivity | Selectivity wt % 1-$C_n$ (n = 4,6,8,10) | Distribution wt % $C_n$ (n = 4,6,8, 10,12,14 and higher) |
| --- | --- | --- | --- | --- | --- |
| 12 |  | 1-hexanol | 1011 | 96,95,95,95 | 31,29,19,11,6,4 |
| 13 |  | 1-octanol | 971 | 97,96,97,96 | 29,29,20,13,6,3 |
| 14 |  | 1-decanol | 743 | 96,95,95,96 | 28,27,19,13,8,5 |
| 15 | TIPP[b] | 1-propanol | 1455 | 97,97,97,97 | 43,30,15,8,3,1 |
| 16 |  | 1-butanol | 1362 | 98,97,96,96 | 41,30,16,9,3,1 |
| 17 |  | 1-pentanol | 1257 | 98,96,97,97 | 40,28,17,9,4,2 |
| 18 |  | 1-hexanol | 1126 | 98,97,97,97 | 37,28,18,10,5,2 |
| 19 |  | 1-octanol | 1018 | 98,97,98,97 | 34,29,18,11,5,3 |
| 20 | TPP[c] | 1-octanol | 434 | 97,96,n/a,n/a | 96,4,0,0,0,0 |

[a]Tricyclohexylphosphine
[b]Triisopropylphosphine
[c]Triphenylphosphine

Table II shows that when an alcohol was used as a solvent for trifluoroacetic acid, the selectivity to 1-olefins was generally higher than 94%.

EXAMPLE III

This example further illustrates ethylene oligomerization in accordance with the invention using an alcohol solvent with the trifluoroacetic acid but using a slightly different procedure than Example II, wherein two reactors are employed rather than only one reactor.

Five milliliters of a 1.9M solution of triethylaluminum (9.50 mmol) in toluene in an argon filled dry box was added to a 40 mL addition vessel followed by pressurizing the vessel to 50 psig with ethylene. The contents of the addition vessel, including the ethylene, were then added to a sealed first reactor which, containing nickel(II) acetylacetonate hydrate (1.390 g; 4.75 mmol), a phosphine compound (4.75 mmol) listed in Table III, and 45 mL of freshly distilled toluene, had been purged with ethylene at least 5 times and pressured with ethylene to 20 psig for 5 minutes. Upon completion of the addition the addition vessel contents to the first reactor, the pressure of the first reactor was maintained at 50 psig with ethylene for 60 minutes to form a homogeneous precursor reaction mixture. All of the above described steps were undertaken at ambient temperature (about 25° C.).

The homogeneous precursor reaction mixture (5 mL) and also the ethylene from the first reactor were then added to a second reactor, containing trifluoroacetic acid (0.450 g; 3.95 mmol) and 35 mL of an alcohol listed in Table III, by the use of a pressure-resistant burette through the addition valve of the second reactor at ambient temperature. After completion of the addition, the second reactor was sealed and pressured to 700 psig with ethylene. The pressure was maintained at 700 psig and temperature at 40° C. for 1 hour as described in Example I. A sample was taken from the second reactor and analyzed, also as described in Example I.

The results, as shown in Table III, show that productivity as high as 3,029 g/g/hr was obtained (run 28) and selectivity to 1-olefins was well over 95%.

TABLE III

| Run | Phosphine | Alcohol Solvent | Productivity | Selectivity: wt % 1-$C_n$ (n = 4,6,8,10) | Distribution wt % $C_n$ (n = 4,6,8, 10,12,14 and higher) |
| --- | --- | --- | --- | --- | --- |
| 21 | TCHP[a] | 1-propanol | 1385 | 97,96,95,95 | 36,30,19,11,3,1 |
| 22 |  | 1-butanol | 1332 | 97,96,96,95 | 35,30,20,11,3,1 |
| 23 |  | 1-pentanol | 1258 | 97,96,96,96 | 34,30,21,11,3,1 |
| 24 |  | 1-hexanol | 930 | 97,96,96,96 | 32,32,20,10,4,2 |
| 25 |  | 1-octanol | 838 | 98,97,98,98 | 30,32,21,11,5,1 |
| 26 |  | 1-decanol | 796 | 98,98,98,98 | 27,31,22,12,5,3 |
| 27 | TIPP[b] | 1-propanol | 2546 | 97,96,98,97 | 42,30,15,8,3,2 |
| 28 |  | 1-butanol | 3029 | 97,97,98,97 | 38,30,17,9,4,2 |
| 29 |  | 1-pentanol | 2329 | 97,97,98,97 | 38,30,17,9,4,2 |
| 30 |  | 1-hexanol | 2457 | 97,97,98,97 | 35,29,18,10,5,3 |
| 31 |  | 1-octanol | 1579 | 97,97,98,98 | 35,29,18,11,5,2 |
| 32 | TPP[c] | 1-octanol | 381 | 97,96,n/a,n/a | 96,4,0,0,0,0 |

[a]Tricyclohexylphosphine
[b]Triisopropylphosphine
[c]Triphenylphosphine

EXAMPLE IV

This example demonstrates ethylene oligomerization employing various alcohol solvents at different reaction times and temperatures, and further employing a single reactor in a variation of the procedure described in Example I.

As noted above, the procedure employed in this example was similar to that employed in Example I, except that nickel(II) acetylacetonate hydrate (0.139 g; 0.47 mmol), a phosphine compound indicated in Table IV (0.47 mmol), 5 mL of freshly distilled toluene and 0.5 mL of 1.9M triethylaluminum solution as added to the addition vessel were subjected to an ethylene pressure of 700 psig for 30 minutes, followed by addition of the contents of the addition vessel, including the ethylene, to a reactor which had been previously charged with trifluoroacetic acid (0.325 g; 2.85 mmol) and 45 mL of the alcohol solvent indicated in Table IV and then pressured to 50 psig. The internal temperature of the reactor during the oligomerization reaction was controlled by external cooling water to the temperature (Rx temp. in °C.) indicated in Table IV. Table IV also indicates the corresponding reaction time (Rx time in minutes) for each run. A sample for analysis was taken from the reactor at end of the reaction period in the manner described in Example I.

TABLE IV

| Run | Phosphine | Alcohol Solvent | Rx Temp. | Rx Time | Productivity | Selectivity wt % 1-$C_{10}$ | Distribution wt % $C_n$ (n = 4,6,8,10,12,14 and higher) |
|---|---|---|---|---|---|---|---|
| 33 | TCHP[a] | 1-hexanol | 36 | 120 | 1071 | 98 | 48,31,14,5,2,0 |
| 34 | | 1-octanol | 35 | 120 | 857 | 98 | 33,29,18,11,6,3 |
| 35 | | 1-decanol | 30 | 60 | 500 | 92 | 31,32,20,10,5,2, |
| 36 | | 2-pentanol | 41 | 30 | 1286 | 93 | 26,31,21,12,6,4 |
| 37 | | t-amyl alcohol[c] | 40 | 30 | 2162 | 92 | 24,28,21,14,8,5 |
| 38 | DCHP[b] | 1-hexanol | 35 | 60 | 584 | 98 | 65,26,7,2,0,0 |
| 39 | | 1-octanol | 36 | 60 | 572 | 98 | 61,28,7,3,1,0 |
| 40 | | 1-decanol | 35 | 60 | 528 | 98 | 52,31,11,4,2,0 |
| 41 | | 2-pentanol | 37 | 120 | 607 | 93 | 43,33,15,6,2,1 |
| 42 | | t-amyl alcohol[c] | 40 | 60 | 1750 | 94 | 28,34,20,11,5,2 |

[a] Tricyclohexylphosphine
[b] Dicyclohexylphosphine
[c] Also known as 2-methyl-2-butanol As can be seen from Table IV, results were favorable insofar as productivities are good, selectivities to 1-olefins are well over 90%, and a good distribution of primarily $C_4$–$C_{10}$ oligomers is indicated.

EXAMPLE V

The purpose of this example is to demonstrate ethylene oligomerization employing a variety of phosphine compounds and a lower (−78° C.) temperature to react the nickel(II) acetylacetonate, phosphine and triethylaluminum.

In a first reactor, 4 mL of a 1.9M triethylaluminum solution in toluene was dropwise added to an ethylene-bubbled (3–5 psig) mixture of nickel(II) acetylacetonate dihydrate (1.113 g; 3.8 mmol), a phosphine (3.8 mmol) listed in Table V and 34 mL of freshly distilled toluene over a period of 3 to 4 minutes under argon atmosphere at −78° C. via the application of an external dry ice/acetone cold bath. 60–90 minutes following completion of the addition of triethylaluminum, 5 mL of the resulting white reaction mixture was transferred to an addition vessel under argon atmosphere and the vessel was sealed and pressured up to 700 psig with ethylene. The contents of the vessel, including the ethylene, were then charged to a second reactor containing freshly distilled trifluoroacetic acid (0.324 g; 3.00 mmol) in 45 mL of 1-octanol wherein reaction continued for 2 hours at a temperature of 40° C. as maintained by cooling water, after which time a sample was taken and analyzed as in Example I. Results are given in Table V.

TABLE V

| Run | Phosphine | Productivity | Selectivity wt % $C_{10}$ | Distribution wt % $C_n$ (n = 4,6,8,10,12,14 and higher) |
|---|---|---|---|---|
| 50 | Tricyclohexylphosphine | 1855 | 96 | 28,24,21,14,10,3 |
| 51 | Triphenylphosphine | 465 | 93 | 67,21,8,3,1,0 |
| 52 | Triethylphosphine | 1294 | 93 | 46,25,16,9,3,1 |
| 53 | Tri-n-butylphosphine | 322 | 92 | 70,21,7,2,0,0 |
| 54 | Tri-t-butylphosphine | 259 | 92 | 65,22,9,3,1,0 |

EXAMPLE VI

This example demonstrates ethylene oligomerization employing a phosphorus-containing compound, a phosphine or phosphite, as an additive to the trifluoroacetic acid.

The runs were similar to those described in Example II with the primary exception that the phosphorus-containing compound (0.945 mmol) listed in Table VI was additionally employed in the addition vessel with the trifluoracetic acid and 1-octanol as the alcohol solvent. A solution of the trifluoracetic acid, 1-octanol and phosphorus compound was charged to the addition vessel with a syringe. In addition, each run employed tricyclohexylphosphine in the reactor in accordance with the procedure of Example II and some runs were conducted at lower temperatures (Rx Temp. in °C.) as shown in Table VI. Results are shown in Table VI.

TABLE VI

| Run | Phosphorus Compound | Rx Temp | Productivity | Selectivity wt % 1-$C_n$ (n = 4,6,8,10) | Distribution wt % $C_n$ (n = 4,6,8,10,12,14 and higher) |
|---|---|---|---|---|---|
| 55 | Triphenylphosphine | 40 | 807 | 97,97,97,97 | 31,29,18,12,6,4 |
| 56 | Tricyclohexylphosphine | 40 | 518 | 97,97,97,97 | 29,29,21,12,6,3 |
| 57 | Tri-n-butylphosphine | 30 | 395 | 100,99,98,98 | 60,26,8,4,2,0 |
| 58 | Diphenylcyclohexylphosphine | 40 | 764 | 99,99,98,98 | 45,30,14,7,3,1 |
| 59 | Dicyclohexylphosphine | 35 | 482 | 100,99,99,98 | 47,30,14,6,2,1 |
| 60 | Triphenylphosphite | 40 | 463 | 97,97,97,97 | 38,31,16,8,4,3 |
| 61 | Triethylphosphite | 40 | 1080 | 99,98,98,98 | 76,18,4,2,0,0 |
| 62 | Tris(2-cyanoethane)phosphine | 34 | 354 | 98,98,98,98 | 31,29,19,12,6,3 |
| 63 | Triisopropyl- | 40 | 977 | 98,99,98,98 | 60,27,9,3,1,0 |

TABLE VI-continued

| Run | Phosphorus Compound | Rx Temp | Productivity | Selectivity wt % 1-$C_n$ (n = 4,6,8,10) | Distribution wt % $C_n$ (n = 4,6,8,10,12,14 and higher) |
|---|---|---|---|---|---|
| 64 | phosphite Trimethylphosphite | 35 | 680 | 100,98,98,n/a | 88,11,1,0,0,0 |

The results indicate that employing the above-mentioned phosphorus compound improved the selectivity to 1-olefins, up to 100% for $C_4$'s in certain runs (runs 57, 59, and 64).

EXAMPLE VII

This example demonstrates the beneficial effect of adding a phosphorus-containing compound, a phosphite or phosphine, to the product reaction mixture after a predetermined reaction time.

In control run 65, the product from run 13 of Example II was distilled to yield the desired fractions. Such fractions were analyzed as discussed previously.

Each of runs 66–74 were carried out to oligomerize ethylene as in Example II with the primary exception that a phosphorus-containing compound (2.0 mmol) listed in Table VII and 1 mL of toluene was charged to a 40 mL addition vessel and pressured to 700 psig, followed by transfer of the resulting solution to the reactor after the reaction had been allowed to continue for about 1 hour. After an additional 5 to 10 minutes, the resulting product was drained from the reactor, of which a sample was analyzed as discussed previously, and distilled to yield the desired fractions. In the case of triphenylphosphite, a precipitate resulted in the product reaction mixture as produced from the reactor which was filtered out by a Buchner filter funnel (40–60μ porosity) prior to distillation. The distilled fractions were also analyzed. Additionally, each run employed tricyclohexylphsophine in the reactor in accordance with the procedure of Example II and 1-octanol as the alcohol solvent for the trifluoroacetic acid.

Results are shown in Table VII.

TABLE VII

| Run | Phosphorus Compound | Selectivity - wt % 1-olefin[a] | | | |
|---|---|---|---|---|---|
| | | 1-$C_6$ | 1-$C_8$ | 1-$C_{10}$ | 1-$C_{12}$ |
| 65 | None | 89(96) | 63(97) | 54(96) | 32(96) |
| 66 | Triphenylphosphine | 94(96) | 88(97) | 82(96) | 79(96) |
| 67 | Tricyclohexylphosphine | 94(96) | 85(97) | 77(96) | 74(96) |
| 68 | Tri-n-propylphosphine | 93(96) | 82(97) | 72(96) | 70(96) |
| 69 | Tri-n-butylphosphine | 94(96) | 86(97) | 84(96) | 80(96) |
| 70 | Trimethylphosphine | 93(96) | 88(97) | 86(96) | 79(96) |
| 71 | Triethylphosphite | 94(96) | 89(97) | 85(96) | 81(96) |
| 72 | Triisopropylphosphite | 94(96) | 85(97) | 82(96) | 80(96) |
| 73 | Tri-n-butylphosphite | 94(96) | 85(97) | 82(96) | 78(96) |
| 74 | Triphenylphosphite | 96(96) | 97(97) | 96(96) | 96(96) |

[a]The values in parentheses are weight percent of 1-olefin before distillation and values out of parentheses are after distillation.

Table VII shows that, without addition of any phosphorus compound to the product reaction mixture according to run 65, selectivity to 1-olefins decreased significantly after distillation, indicating isomerization of 1-olefins to other isomers during distillation. This was especially significant for higher olefins. Upon addition of a phosphorus compound according to runs 66–74, the weight percent of 1-olefins after distillation improved significantly. Run 74 further shows that triphenylphosphite is the preferred phosphorus compound insofar as it completely prevents isomerization during distillation. It was also discovered that, upon the addition of the triphenylphosphite and as discussed above, at least a portion of the nonoligomer components of the product reaction mixture precipitated out with the triphenylphosphite. The precipitation therefore facilitates the separation and recovery of the oligomerization product from the product reaction mixture.

EXAMPLE VIII

Comparative

The purpose of this example is to demonstrate that without the addition of trifluoroacetic acid, oligomerization does not occur under the same process conditions in which addition of the acid does result in production of oligomers.

A run was carried out which was the same as run 2 of Example I, except that no trifluoroacetic acid was added to the reactor. A reactor internal pressure of 700 psig and a reaction temperature of 40° C. was maintained for 2 hours, after which period a sample was taken from the reactor and analyzed as in Example I. No oligomers were detected thereby giving a productivity of 0.

That which is claimed is:

1. A process for oligomerizing ethylene to an oligomerization product comprising:
   (a) contacting ethylene; an organonickel(II) compound selected from the group consisting of bis(cyclopentadienyl) nickel (II), bis(pentamethylcyclopentadienyl) nickel(II), nickel(II) 2-ethylhexanoate, nickel(II) acetylacetonate, nickel(II) hexafluoroacetylacetonate, and nickel(II) trifluoroacetylacetonate; a phosphine compound of the formula $PR_3$ where R independently represents H or a $C_1$ to $C_{20}$ hydrocarbyl radical and where at least one R is not H; and a trialkylaluminum compound of the formula $AlR'_3$ where R' represents a $C_1$ to $C_{12}$ alkyl radical; wherein the ethylene is in a gaseous phase and the organonickel(II) compound, phosphine compound, and trialkylaluminum compound are in a solvent and in a liquid phase, thereby producing a precursor reaction mixture in a liquid phase; and
   (b) contacting, after step (a), ethylene in a gaseous phase; the precursor reaction mixture; and a fluorinated carboxylic acid in a liquid phase and of the formula R"COOH where R" represents a $C_1$ to $C_{10}$ hydrocarbyl radical having at least one fluorine (F) atom; thereby producing a product reaction mixture in a liquid phase comprising the oligomerization product.

2. A process as recited in claim 1 wherein step (a) is carried out at a pressure of about 5 to about 5000 psig, at a temperature of about −100° C. to about 50° C., and for a time of about 1 minute to about 6 hours.

3. A process as recited in claim 2 wherein step (a) is carried out at a pressure of about 20 to about 1000 psig, 4. A process as recited in claim 1 wherein step (b) is carried out at a pressure of about 5 to about 5000 psig, at a temperature of about 0° C. to about 125° C., and for a time of about 1 minute to about 15 hours.

5. A process as recited in claim 4 wherein step (b) is carried out at a pressure of about 200 to about 1000 psig, at a temperature of about 20° C. to about 50° C., and for a time of about 15 minutes to about 5 hours.

6. A process as recited in claim 1 wherein the fluorinated carboxylic acid is contacted with ethylene prior to step (b).

7. A process as recited in claim 1 wherein the organonickel(II) compound is nickel(II) acetylacetonate.

8. A process as recited in claim 1 wherein the phosphine compound is selected from the group consisting of triisopropylphosphine and tricyclohexylphosphine.

9. A process as recited in claim 1 wherein the trialkylaluminum compound is triethylaluminum.

10. A process as recited in claim 1 wherein the molar ratio of (i) the phosphine compound, (ii) the trialkylaluminum compound, and (iii) the fluorinated carboxylic acid, respectively, to the organonickel(II) compound are as follows: (i) about 0.1 to 5 to 1; (ii) about 1–10 to 1; and (iii) about 1–20 to 1.

11. A process as recited in claim 1 wherein said solvent in step (a) is hereafter denoted as a first solvent and is selected from the group consisting of: a saturated hydrocarbon or fluorinated hydrocarbon of the formula $C_nH_{2n+2-x}F_x$ where n=4, 5, 6, 7 or 8 and x=0, 1 or 2; and an aromatic hydrocarbon or fluorinated hydrocarbon of the formula $C_6H_{6-n}(R''')_n$, where n=0, 1, 2, 3 or 4 and $R'''$ independently represents F or a $C_1$ to $C_6$ alkyl radical or fluorinated alkyl radical.

12. A process as recited in claim 11 wherein the fluorinated carboxylic acid in step (b) is in a second solvent which is selected from the group consisting of: said saturated hydrocarbon or fluorinated hydrocarbon; said aromatic hydrocarbon or fluorinated hydrocarbon; and an alcohol of the formula $(R^{iv})_3COH$ where $R^{iv}$ independently represents H, F or a $C_1$ to $C_{12}$ alkyl, cycloalkyl, aryl, alkaryl, or aralkyl radical and where at least one $R^{iv}$ is neither H nor F.

13. A process as recited in claim 12 wherein the first solvent is said aromatic hydrocarbon and the second solvent is said alcohol.

14. A process for oligomerizing ethylene to an oligomerization product comprising:
(a) contacting ethylene; an organonickel(II) compound selected from the group consisting of bis(cyclopentadienyl) nickel(II), bis(pentamethylcyclopentadienyl) nickel(II), nickel(II) 2-ethylhexanoate, nickel(II) acetylacetonate, nickel(II) hexafluoroacetylacetonate, and nickel(II) trifluoracetylacetonate; a phosphine compound of the formula $PR_3$ where R independently represents H or a $C_1$ to $C_{20}$ hydrocarbyl radical and where at least one R is not H; and a trialkylaluminum compound of the formula $AlR'_3$ where $R'$ represents a $C_1$ to $C_{12}$ alkyl radical; wherein the ethylene is in a gaseous phase and the organonickel(II) compound, phosphine compound, and trialkylaluminum compound are in a solvent and in a liquid phase, thereby producing a precursor reaction mixture in a liquid phase; and
(b) contacting, after step (a), ethylene in a gaseous phase; the precursor reaction mixture; and a fluorinated carboxylic acid in a liquid phase and of the formula R"COOH where R" represents a $C_1$ to $C_3$ hydrocarbyl radical having at least one fluorine (F) atom; thereby producing a product reaction mixture in a liquid phase comprising the oligomerization product.

15. A process for oligomerizing ethylene to an oligomerization product comprising:
(a) contacting ethylene; an organonickel(II) compound selected from the group consisting of bis(cyclopentadienyl) nickel(II), bis(pentamethylcyclopentadienyl) nickel(II), nickel(II) 2-ethylhexanoate, nickel(II) acetylacetonate, nickel(II) hexafluoroacetylacetonate, and nickel(II) trifluoroacetylacetonate; a phosphine compound of the formula $PR_3$ where R independently represents H or a $C_1$ to $C_{20}$ hydrocarbyl radical and where at least one R is not H; and a trialkylaluminum compound of the formula $AlR'_3$ where $R'$ represents a $C_1$ to $C_{12}$ alkyl radical; wherein the ethylene is in a gaseous phase and the organonickel(II) compound, phosphine compound, and trialkylaluminum compound are in a solvent and in a liquid phase, thereby producing a precursor reaction mixture in a liquid phase; and
(b) contacting, after step (a), ethylene in a gaseous phase; the precursor reaction mixture; and trifluoracetic acid in a liquid phase; thereby producing a product reaction mixture in a liquid phase comprising the oligomerization product.

16. A process for oligomerizing ethylene to an oligomerization product comprising:
(a) contacting ethylene, nickel(II) acetylacetonate, a phosphine compound of the formula $PR_3$ where R independently represents H or a $C_1$ to $C_{20}$ hydrocarbyl radical and where at least one R is not H, and triethylaluminum, wherein the ethylene is in a gaseous phase and the nickel(II) acetylacetonate, phosphine compound, and triethylaluminum are in a solvent and in a liquid phase, thereby producing a precursor reaction mixture in a liquid phase; and
(b) contacting, after step (a), ethylene in a gaseous phase, the precursor reaction mixture, and trifluoroacetic acid in a liquid phase, thereby producing a product reaction mixture in a liquid phase comprising the oligomerization product.

17. A process for oligomerizing ethylene to an oligomerization product comprising:
(a) contacting ethylene; an organonickel(II) compound selected from the group consisting of bis(cyclopentadienyl) nickel(II), bis(pentamethylcyclopentadienyl) nickel(II), nickel(II) 2-ethylhexanoate, nickel(II) acetylacetonate, nickel(II) hexafluoroacetylacetonate, and nickel(II) trifluoroacetylacetonate; a phosphine compound of the formula $PR_3$ where R independently represents H or a $C_1$ to $C_{20}$ hydrocarbyl radical and where at least one R is not H; and a trialkylaluminum compound of the formula $AlR'_3$ where R represents a $C_1$ to $C_{12}$ alkyl radical; wherein the ethylene is in a gaseous phase and the organonickel(II) compound, phosphine compound, and trialkylaluminum compound are in a first solvent and in a liquid phase, thereby producing a precursor reaction mixture in a liquid phase; and
(b) contacting, after step (a), ethylene in a gaseous phase; the precursor reaction mixture; and a fluorinated carboxylic acid in a second solvent and in a liquid phase, wherein the fluorinated carboxylic acid is of the formula R"COOH where R" represents a $C_1$ to $C_{10}$ hydrocarbyl radical having at least one fluorine (F) atom, and wherein there is also present in the second solvent a phosphorus-containing compound selected from the group consisting of (i) a phosphine compound of the formula $PR_3$ where R independently represents H or a $C_1$ to $C_{20}$ hydrocarbyl radical and where at least one R is not H, and (ii) a phosphite compound of the formula $P(OR^v)_3$ where $R^v$ independently represents H or a $C_1$ to $C_{20}$ hydrocarbyl radical and where at least one $R^v$ is not H; thereby producing a product reaction mixture in a liquid phase comprising the oligomerization product.

18. A process as recited in claim 17 wherein the molar ratio of the phosphorus-containing compound to the organonickel(II) compound is about 0.1–10 to 1.

19. A process for oligomerizing ethylene to an oligomerization product comprising:

(a) contacting ethylene; an organonickel(II) compound selected from the group consisting of bis(cyclopentadienyl) nickel(II), bis(pentamethylcyclopentadienyl) nickel(II), nickel(II) 2-ethylhexanoate, nickel(II) acetylacetonate, nickel(II) hexafluoroacetylacetonate, and nickel(II) trifluoroacetylacetonate; a phosphine compound of the formula $PR_3$ where R independently represents H or a $C_1$ to $C_{20}$ hydrocarbyl radical and where at least one R is not H; and a trialkylaluminum compound of the formula $AlR'_3$ where R' represents a $C_1$ to $C_{12}$ alkyl radical; wherein the ethylene is in a gaseous phase and the organonickel(II) compound, phosphine compound, and trialkylaluminum compound are in a solvent and in a liquid phase, thereby producing a precursor reaction mixture in a liquid phase;

(b) contacting, after step (a), ethylene in a gaseous phase; the precursor reaction mixture; and a fluorinated carboxylic acid in a liquid phase and of the formula R"COOH where R" represents a $C_1$ to $C_{10}$ hydrocarbyl radical having at least one fluorine (F) atom; thereby producing a product reaction mixture in a liquid phase comprising the oligomerization product; and (c) contacting the product reaction mixture with a phosphorus-containing compound at a predetermined time following the commencement of step (b), wherein the phosphorus-containing compound is selected from the group consisting of (i) a phosphine compound of the formula $PR_3$ where R independently represents H or a $C_1$ to $C_{20}$ hydrocarbyl radical and where at least one R is not H, and (ii) a phosphine compound of the formula $P(OR^v)_3$ where $R^v$ independently represents H or a $C_1$ to $C_{20}$ hydrocarbyl radical and where at least one $R^v$ is not H.

20. A process as recited in claim 19 wherein the molar ratio of the phosphorus-containing compound to the organonickel(II) compound is about 0.5–10 to 1.

21. A process as recited in claim 20 wherein the phosphorus-containing compound is triphenylphosphite.

* * * * *